US005641498A

United States Patent [19]

Loosemore

[11] Patent Number: 5,641,498
[45] Date of Patent: Jun. 24, 1997

[54] GERMICIDAL TEAT DIP COMPOSITION

[75] Inventor: Michael J. Loosemore, Auburn, Mass.

[73] Assignee: IBA, Inc., Millbury, Mass.

[21] Appl. No.: 529,236

[22] Filed: Sep. 15, 1995

[51] Int. Cl.$^6$ ................................................. A01N 25/24
[52] U.S. Cl. .................. 424/405; 424/78.17; 424/78.18; 424/407
[58] Field of Search ................. 424/405, 78.17, 424/78.18, 407; 514/772.2; 524/503; 525/56, 62, 61

[56] References Cited

U.S. PATENT DOCUMENTS

| | | | |
|---|---|---|---|
| 4,113,854 | 9/1978 | Andrews et al. | 424/78.05 |
| 5,017,369 | 5/1991 | Marhevka | 424/407 |
| 5,211,961 | 5/1993 | Adkinson | 424/616 |

*Primary Examiner*—Melvyn I. Marquis
*Assistant Examiner*—Robert H. Harrison
*Attorney, Agent, or Firm*—Terry M. Crellin

[57] ABSTRACT

Skin sanitizing compositions useful for disinfecting of teat skin surfaces of dairy cows form and provide a provide a protective germicidal barrier film on the skin surface and plug the mammary canal. These compositions comprise aqueous solutions containing a film forming polymer, a plasticizing agent, buffering agents, skin conditioners and a germicide. The compositions provide a germicidal film which acts also as a barrier to skin moisture loss which can be completely removed when desired. A preferred embodiment of the composition contains an opacifying agent.

13 Claims, No Drawings

GERMICIDAL TEAT DIP COMPOSITION

FIELD OF INVENTION

This invention relates to new germicidal compositions useful for sanitizing skin and providing a physical barrier to protect skin by preventing and/or retarding the reintroduction of pathogenic organisms and extraneous material into skin contact.

BACKGROUND AND PRIOR ART

The invention is particularly directed towards the germicidal disinfecting of the skin surfaces on dairy cow teats and additionally providing a germicidal barrier film such that the disinfected teat skin is physically protected from the unhindered reintroduction of pathogens back onto the teat skin surface and such that a plug of this film is formed at the opening of the mammary sphincter providing protection from the introduction of pathogenic organisms into the mammary canal. The control of pathogenic organisms on the teat skin of dairy cows is a major goal of the dairy industry. Contact with the bovine mammary gland by a pathogenic microorganism, usually bacteria but occasionally yeast or fungi, can result in the disease of mastitis. Mastitis is a serious infection which can in severe cases, cause death to the dairy cow and even in much milder cases can result in long term damage to the cow, loss of milk production for the dairy farmer and overall an unacceptable increase in costs to the farmer. Mastitis is indeed widely considered to be the single most costly disease in the dairy industry. Efforts to control the presence of infectious agents date back to the early 1900's but the success of these efforts was limited by the unavailability of effective germicidal agents. The incidence of mastitis has decreased over the last twenty-five years due to the realization that proper hygiene, particularly with regard to the udder and teat surfaces of the cow is very important and due to the widespread acceptance of the practice of dipping the cows teats in a germicidal agent after milking.

Modern vacuum milking machines have perhaps made teat dipping more critical. Vacuum milking causes a relaxation of the sphincter muscle at the end of the teat canal resulting in an open canal which may require several minutes to hours to contract and close. This open period proffers a direct access route, a veritable highway for microbes, leading to the mammary gland. Dipping the teat in a disinfectant immediately after milking has been shown to be an economical and effective measure in helping to reduce the incidence of mastitis infection. Many disinfectant agents have been used in teat dips, among them: iodine, chlorine, chlorine dioxide, chlorhexidine, fatty acids, anionic surfactants and quaternary ammonium compounds.

These disinfectant agents are generally useful for helping to reduce the bacterial population on the teat skin. Mastitis still persists as the significant dairy cow disease which indicates that the current products do not address all areas of concern. It is an ironic twist that some of the available teat dip agents, notably Iodine and Chlorine, may in fact, contribute to the mastitis problem by causing irritation of the teat skin, thus providing an opportunistic site which promotes infection. Many available teat dip formulations attempt to combat this potential for irritation by incorporating emollient agents in an effort to soothe the skin. Additionally, some of the more powerful disinfectants, chlorine for example, can be particularly noxious for the user as well. Others such as fatty acids and anionic surfactants are not broad enough in their antibacterial spectrum to provide complete protection. Regardless of which germicidal agent is employed or how it is formulated, the ultimate objective of teat sanitation is to minimize teat contamination for as long as possible. It is on this point that conventional teat dips fail. Once germicidal activity of the teat dip ceases, there is no control of environmental pathogens which may be encountered by the teat skin and open mammary canal.

Recent product developments have sought to provide better environmental pathogen protection by bringing forth new teat dips referred to as barrier dips. These products seek to provide an antimicrobial agent, as well as, a coating for the teat skin and a plugging of the open teat canal. One of these products has provided an effective covering of the teat with a latex material (U.S. Pat. No. 4,113,854). This however, has the serious drawback of not being readily removable when the next milking time arrives. The result can be a partially removed coating, leaving behind particles to become trapped in the milk line filters. The difficulties of removal can further result in excessive rubbing of the teat skin, thus leading to irritation. Some of the coating agents tried contain irritants and solvents such as ammonia and even latex has come into question of late due to allergic irritation in human use. Still other products have relied upon weaker antimicrobial agents such as anionic surfactants (U.S. Pat. No. 4,376,787) or are active only at low non-physiological pH values.

There are also barrier products which are essentially thickened teat dips which leave behind a deposit such as cellulose upon drying. These products lack flexibility and tend to crack and flake off, seriously compromising any barrier function by not providing a continuous film of protection. Those products which rely upon a potentially irritating germicide such as iodine must address the potential for skin irritation upon drying which potentially prolongs the iodine contact time and irritation of teat skin. One such product relies upon chlorine dioxide as the germicidal agent. This product has the disadvantages of being a two-part system requiring accurate premixing in the field, of operating at a low non-physiological pH and of losing its germicidal activity over time once it is mixed.

OBJECTIVES AND BRIEF DESCRIPTION OF INVENTION

A principal objective of the present invention is to provide a simple to use one-part film forming germicidal barrier teat dip.

Another objective of the present invention is to provide a plugging film at the opening of the mammary canal.

Another objective of the present invention is to provide an easy to remove, non-toxic, non-irritating, barrier film of variable and controllable water solubility.

Another objective of the present invention is to provide an adherent, flexible antimicrobial barrier film which will afford physical protection to the teat skin from abrasion and environmental physical irritants.

Another objective of the present invention is to provide a pathogen resistant film to inhibit the transmission of environmental organisms capable of causing mastitis such as airborne or pestborne pathogens.

Another objective of the present invention is to provide a means to control the critical skin moisture retention on the cows teat skin, particularly under dehydrating conditions of low relative humidity.

Another objective of the present invention is to provide a barrier film containing an integral incorporation of germicidal agent.

Another objective of the present invention is to provide prolonged germicidal protection for dairy cow teats between milking periods.

Another objective of the present invention is to provide a true platicitable film which may contain and is compatible with antimicrobial agents.

Another objective of the present invention is to provide formulations for a germicidal barrier teat dip.

It has been discovered in this invention that the utilization of a plasticized polymer, polyvinyl alcohol film, incorporating an established germicidal agent such as chlorhexidine provides an effective barrier film teat dip. The unique gas permeation properties of the polymer film allow gas permeability of the film to decrease as the ambient relative humidity decreases. Thus, at low relative humidity gas transport is hindered helping to retain moisture at the teat skin, effectively contributing to emolliency of the product. Additionally, the incorporation of humectants in the formulation of this invention allows for further moisture retention and skin conditioning. This invention does not rely upon the deposition of thickened material but rather provides a true plasticized film barrier which can be viscosity controlled to allow formation of a drop like plug at the end of the cow's teat. The formulations of this invention provide a durable, flexible and adherent film which can be easily removed when desired by simple washing of the cow teats prior to milking. The ingredients of this invention are non-toxic and non-irritating. The incorporation of a germicidal agent into the film formed by this invention provides a long lasting germicidal active teat skin covering during that vulnerable period between milkings.

Topically applied compositions of this invention have been tested according to National Mastitis Council Protocol A and shown to have excellent antimicrobial activity. The compositions of this invention have been and will be described as teat dips though, of course, other topical methods of application may be used provided they produce an effective antimicrobial barrier.

DETAILED DESCRIPTION OF THE PREFERRED EMBODIMENTS

The germicidal barrier composition of the present invention comprises a diluent and from about 2% to about 10% by weight of a barrier film forming polymer consisting essentially of polyvinyl alcohol. In addition, the composition of the present invention includes from about 0.3% to about 1% by weight of a germicidal agent comprising chlorhexidine salt. The germicidal agent is also referred herein as an antimicrobial agent. The composition of the invention also includes from about 1% to about 8% by weight of a plasticizing agent and from about 1.5% to about 5% by weight of a compatible surfactant. Additional ingredients of the composition of the present invention preferably include buffering agents, skin conditioners, viscosity control agents, film property modifiers and other ingredients. Each of the ingredients of the composition of the present invention will be further discussed hereinafter under an appropriate heading for each such ingredient.

DILUENT

The preferred diluent in the compositions of this invention is water. Water has inherent economic advantages over other possible liquid diluents and it provides a safe non-toxic, non-irritating vehicle with sufficient volatility to assist in the barrier film formation properties of this invention.

ANTIMICROBIAL AGENT

The preferred antimicrobial agent for formulation of this invention is any of the water soluble salts of chlorhexidine (N,N"-Bis(4-chlorophenyl)-3,12-diimino -2,4,11,13 tetradecanediimidamide). Each of the salts formed as the diacetate, digluconate or diphosphate are acceptable for use at levels of 0.3–1.0% by weight of the formulation.

SURFACTANTS

The surfactant must be compatible with the formulation components of this invention in particular the barrier film forming agent polyvinyl alcohol and the germicidal agent most preferably chlorhexidine digluconate. The surfactant must also assist in the desired removal of the barrier film by functioning as a rewetting agent. The surfactants used in this invention are typically nonionic of the type:

$$R\text{-}O\text{-}(C_2H_4O)_n\text{-}H$$

Where R can be an octyl or aonyl phenol or a primary or secondary alcohol of C-C22 and n can be from 4–30 or of the type:

alpha-hydroxy-omega-hydroxy-poly (oxyethylene) poly (oxypropylene) poly (oxyethylene) block co-polymer such that the poly (oxyethylene) component is 10–40% of the total molecule by weight.

BARRIER FILM FORMING AGENTS

The barrier film forming agents used are such as to provide good flexibility, structural integrity and to make a maximum contribution to the barrier function. Similarly the water solubility of the film must be such that it provides barrier and germicidal effectiveness but also that the film can be easily and completely removed when needed. The agents used in this invention are of the polyvinyl alcohol type between 86–99% hydrolyzed and being of the medium to high viscosity molecular weight, that is between 20 and 90 CPS for a 4% solution. The preferred polyvinyl alcohols for this invention are for the high molecular weight type preferably 98% or greater hydrolysis percent and viscosity of greater than 60 CPS at 4% and for the medium range molecular weight preferably 95% or greater hydrolysis with a viscosity of greater than 20 but less than 40 CPS at 4%.

SKIN CONDITIONERS

Emollients and humectants incorporated into compositions of the present invention serve to assist in soothing and retaining moisture on the skin. A conditioner to be useful for this invention must be compatible with the other ingredients and not detract from the antimicrobial or skin barrier performance of the invention. Many polyglycols, sorbitol aloe and lanolin have been found to be compatible. The preferred skin conditioners for use in practicing this invention are a combination of glycerin and propylene glycol in a ratio of 0.1:1 to 1:1 with a total content between 0.2 and 20%. The barrier film described in this invention when composed as described functions itself as an emollient type skin conditioner. The most preferred ratio being about 0.8:1 at a total level of between 8–12%.

VISCOSITY CONTROL AGENTS

The viscosity of the invention can be influenced by the addition of standard thickeners such as cellulose derivatives, however, to best preserve the properties of the barrier film the preferred method of viscosity control has been shown to be through variation of the polyvinyl alcohols incorporated within the formulation. The preferred level and ratio of polyvinyl alcohols was chosen to produce a viscosity which will leave an adequate amount of product when applied to the teat but not to be overly viscous such as to make application difficult by dipping or other methods. Typically incorporation of 2 to 10% of polyvinyl alcohol with a ratio of high viscosity to medium viscosity polyvinyl alcohol of between 0.1:1 and 1:2 is sufficient with a preferred level of 2 to 8% total polyvinyl alcohol at a ratio of high viscosity to medium viscosity of 0.5:1 to 0.8:1 and a finished product viscosity of between 100 and 500 CPS.

FILM PROPERTY MODIFIERS

As has been previously described, the water solubility of the germicidal barrier film resultant from this invention can be controlled by varying the ratio of various polyvinyl alcohol polymers employed. It is also important for flexibility and integrity of the germicidal barrier that the resultant film be plasticized. Plastization of the film has been accomplished for the purposes of this invention by the incorporation of a suitable plasticizing agent such as solvents and or polyols. It has been have found that glycerin at levels of 1 to no more than 8 percent is the most suitable agent for the purposes of this invention. However, polyethylene glycols of the type PEG200-PEG800 and Sorbitol also will function as plasticizing agents at 2-8%.

BUFFERING AGENTS

Buffering agents utilized in this invention include the acid form and base salt of an organic or inorganic acid in such ratio as to produce a resultant pH value for the finished formulation of 5-7. The acids lactic, citric, gluconic, acetic and phosphoric have been used with the citric/citrate combination at pH 5.8 to 6.2 at a total use level of 0.5% by weight of the formulation being preferred.

OTHER INGREDIENTS

It has been found that the dried barrier film formed by use of this invention can be better visualized when colored and or opacified. This saves duplication of effort by the farmer and assists in identifying complete film removal when required. The preferred dyes used for this invention include but are not limited to FD&C Blue No. 1. Various opacifiers were found to be effective, including bentonite clays, colloidal silicas, stearyl amides, stearyl esters and Aluminum and Magnesium stearates. The preferred embodiment of this invention includes stearyl amide at 0-5% by weight of the total formulation.

EXAMPLES

Three examples of antimicrobial compositions in accordance with the present invention were prepared. The ingredients for each example are set forth in Table 1 in percent by weight.

TABLE 1

| Ingredient | Example 1 | Example 2 | Example 3 |
| --- | --- | --- | --- |
| Polyvinyl Alcohol Medium Viscosity | 0.0 | 3.0 | 3.0 |
| Polyvinyl Alcohol High Viscosity | 0.0 | 2.0 | 2.0 |
| Stearyl Diethanol Amide | 0.0 | 0.0 | 1.0 |
| Alcohol Ethoxylate | 1.5 | 1.5 | 1.5 |
| Glycerin | 4.0 | 4.0 | 4.0 |
| Propylene Glycol | 0.0 | 0.0 | 5.0 |
| Citric Acid | 0.08 | 0.08 | 0.08 |

TABLE 1-continued

| Ingredient | Example 1 | Example 2 | Example 3 |
| --- | --- | --- | --- |
| Sodium Citrate | 4.42 | 0.42 | 0.42 |
| Chlorhexidine Digluconate | 0.6 | 0.6 | 0.6 |
| Water | 93.4 | 88.4 | 82.4 |

The formulations were prepared by first dissolving the polyvinyl alcohol in hot water with vigorous stirring, taking care to avoid foam formation throughout. Stearyl amide was next added while the water temperature was above 115° F., the mixture is agitated continuously and when the temperature drops below 90° F. the other components 4 through 9 are added in order. The final pH is adjusted to 5.8–6.2 with the further addition of citric acid or sodium hydroxide, if necessary.

Each of compositions from Examples 1 through 3 was evaluated for antimicrobial activity against Staphylococcus Aureus and Streptococcus Agalactiae in accordance with testing Protocol A of the National Mastitis Council, and compared to a negative control and a standard 1% iodine teat dip. Excised cow teats are dipped in a suspension of challenge organisms at a level of about $1 \times 10^8$ colony forming units/ml and then dipped in a germicidal composition. A negative control was used as was a standard 1% iodine product. The results are summarized in Table 2 as the percentage reduction of surviving organisms relative to the control.

TABLE 2

| | Challenge Organism % Reduction | |
| --- | --- | --- |
| Composition | Streptococcus Agalactiae | Staphylococcus Aureus |
| Negative Control | 00.000 | 00.000 |
| 1% Iodine | 99.951 | 99.989 |
| Of Example 1 | 99.996 | 99.999 |
| Of Example 2 | 99.991 | 99.999 |
| Of Example 3 | 99.999 | 99.997 |

The results as shown in Table 2 clearly indicate that neither the opacifier polyvinyl alcohol nor humectant compromises the germicidal activity of the formulation and the active antimicrobial agent chlorhexidine digluconate. The results further show that the complete barrier teat dip of the type described in this invention is as germicidal as the widely accepted 1% iodine teat dip.

The composition of Example 3 was then tested for antimicrobial effectiveness against a number of pertinent organisms. Suspensions of the respective organisms were diluted 1:1 with the composition of Example 3 to an approximate concentration of $1 \times 10^8$ organisms/ml. The organisms were incubated for 30 seconds at which point 1.0 ml samples were cultured. The original bacterial suspensions were diluted 1:1 with sterile saline and 1.0 microliter was cultured as a positive control. The results of this testing as shown in Table 3 indicates clearly that the formulation of this invention exhibits broad spectrum antimicrobial ability.

TABLE 3

| Organisms | Colony Forming Units | |
|---|---|---|
|  | Control | Composition of Example 3 |
| *Escherichia Coli* | 1.2 × 10⁸ | None |
| *Staphylococcus Aureus* | 1.1 × 10⁸ | None |
| *Pseudomonas Aeruginosa* | 8 × 10⁷ | None |
| *Streptococcus Uberis* | 1.5 × 10⁸ | None |
| *Streptococcus Agalactiae* | 1.3 × 10⁸ | None |
| *Streptococcus Dysagalactiae* | 1.1 × 10⁸ | None |
| *Enterobacter Aerogenes* | 9 × 10⁷ | None |
| *Klebsiella Pneumoniae* | 9 × 10⁷ | None |

Finally, the barrier teat dip of this invention was evaluated for its effectiveness for maintaining healthy teat skin in field use. The composition of Example 3 was subjected to the standard teat score test by which the physical improvement of the skin of the cow's teats was evaluated after one month of use of the composition of Example 3. In this evaluation, 13 cows were treated with a the composition of Example 3 for a period of one month. The condition of the teat skin was evaluated just prior to the use of the composition and again at the conclusion of the one month period of treatment. The skin condition was scored such that a rating of 1.0 is considered normal healthy skin. Higher numbers are assigned when there are signs of irritation or damage up to a rating of 5.00 for severely damaged skin with open lesions. The highly favorable results are summarized in Table IV.

TABLE 4

| | |
|---|---|
| Number of cows treated | 13 |
| Number of cows teat skin condition worsened | 0 |
| Number of cows teat skin condition improved | 13 |
| Average numerical skin rating at the start of study | 1.6 |
| Average numerical skin rating at conclusion of study | 1.0 |
| Average improvement in skin rating | 0.6 (improved) |

We claim:

1. A germicidal barrier composition for application to the teat of a cow, said composition comprising from about 2% to about 10% by weight of a barrier film forming polymer consisting essentially of polyvinyl alcohol, from about 0.3% to about 1% by weight of a germicidal agent comprising chlorhexidine salt, from about 1% to about 8% by weight of a plasticizing agent, and from about 0.5% to about 5% by weight of a compatible surfactant, said polyvinyl alcohol consisting of a blend of high viscosity type polyvinyl alcohol and medium viscosity type polyvinyl alcohol, with the high viscosity type having a degree of hydrolysis of between about 98% to about 99% and a viscosity of between about 60 centipoise and about 80 centipoise at 4% aqueous solution and the medium viscosity type having a degree of hydrolysis of between about 95% and about 97% and a viscosity of between about 25 centipoise and about 35 centipoise at 4% aqueous solution, and further wherein the ratio of high viscosity type to medium viscosity type is between about 1:3 and 3:1.

2. A germicidal barrier composition as in claim 1 wherein the ratio of high viscosity type polyvinyl alcohol to medium viscosity type polyvinyl alcohol is about 2:3.

3. A germicidal barrier composition as in claim 1, wherein said composition contains from about 4% to about 8% by weight polyvinyl alcohol, and further wherein said composition contains a suitable buffering agent to provide a finished composition pH of from about 5 to about 7.

4. A germicidal barrier composition as in claim 3, wherein the plasticizing agent is glycerin and said composition contains said glycerin in an amount of from about 1% to about 8% by weight.

5. A germicidal barrier composition as in claim 4 further containing from about 1% to about 10% by weight of a humectant skin conditioning agent that is selected from the group consisting of propylene glycol sorbitol and lanolin.

6. A germicidal barrier composition as in claim 5, wherein said composition further includes a buffering agent that is selected from the group consisting of acetic, citric, gluconic, phosphoric, tartaric and malic acids and the salts of those acids.

7. A germicidal barrier composition as in claim 6, wherein said composition contains from about 0.5% to about 2% by weight of said buffering agent, said buffering agent being selected from the group consisting of citric acid, sodium citrate and potassium citrate.

8. A germicidal barrier composition as in claims 5 or 6, wherein the germicidal agent is selected from the group consisting of chlorhexidine digluconate, chlorhexidine diacetate and chlorhexidine diphosphate.

9. A germicidal barrier composition as in claims 5 or 6, wherein the germicidal agent is chlorhexidine digluconate.

10. A germicidal barrier composition as in claims 5 or 6, wherein the germicidal agent is chlorhexidine diacetate.

11. A germicidal barrier composition as in claims 5 or 6, wherein the germicidal agent is chlorhexidine diphosphate.

12. A germicidal barrier composition as in claim 7, wherein said composition contains an opacifying agent.

13. A germicidal barrier composition as in claim 12, wherein said opacifying agent is stearyl diethanol amide.

* * * * *